United States Patent [19]

Ofstead et al.

[11] 4,155,943
[45] May 22, 1979

[54] HYDROGENATION USING SURFACTANTS

[75] Inventors: Eilert A. Ofstead, Cuyahoga Falls; Lawson G. Wideman, Akron, both of Ohio

[73] Assignee: The Goodyear Tire & Rubber Company, Akron, Ohio

[21] Appl. No.: 850,581

[22] Filed: Nov. 11, 1977

[51] Int. Cl.² ............................................. C07C 5/06
[52] U.S. Cl. ................................................... 585/274
[58] Field of Search .............. 260/666 A, 683.9, 683.2

[56] References Cited

U.S. PATENT DOCUMENTS

| | | | |
|---|---|---|---|
| 2,360,555 | 10/1944 | Evans et al. | 260/666 A |
| 3,213,155 | 10/1965 | Schriesheim et al. | 260/683.2 |
| 3,217,050 | 11/1965 | Schriesheim et al. | 260/668 R |
| 3,270,084 | 8/1966 | Schriesheim et al. | 260/683.2 |
| 3,637,877 | 1/1972 | Nowack et al. | 260/666 A |
| 3,937,745 | 2/1976 | Wideman et al. | 260/666 A |

*Primary Examiner*—Veronica O'Keefe
*Attorney, Agent, or Firm*—J. Y. Clowney

[57] ABSTRACT

There is disclosed a process for the preparation of cyclopentene which comprises selectively hydrogenating cyclopentadiene in the liquid phase by contacting cyclopentadiene with hydrogen in the presence of a hydrogenation catalyst comprising a highly dispersed form of nickel in which a substantial amount of water and certain surfactants are employed in the reaction mixture.

2 Claims, No Drawings

HYDROGENATION USING SURFACTANTS

BACKGROUND OF THE INVENTION

This invention is directed to the selective hydrogenation of dienes to monoolefins particularly of cyclopentadiene to cyclopentene. More specifically, it is directed to a process whereby cyclopentadiene is selectively hydrogenated to cyclopentene through the use of a highly dispersed form of nickel as a catalyst and in which a substantial amount of water and certain surfactants are used as a reaction medium. The surfactants employed are anionic surfactants, cationic surfactants, non-ionic surfactants, amphoteric surfactants, naturally occurring surfactants and oil soluble surfactants.

At the present time, substantial amounts of cyclopentadiene, usually as dicyclopentadiene, are available as a byproduct from the steam cracking of naphtha to produce primarily ethylene. Cyclopentene has been found to be useful as a monomer for the formation of general purpose elastomers by ring opening polymerization of cyclopentene. Therefore, it is desirable to convert a portion of the excess cyclopentadiene available into a more valuable raw material, such as cyclopentene.

The hydrogenation of cyclopentadiene to cyclopentene is not new. For instance, in U.S. Pat. No. 2,360,555 issued Oct. 17, 1944, there is disclosed a selective hydrogenation of one of the two conjugated double bonds of a cyclic diolefin to produce the corresponding cyclic monoolefin which is accomplished by conducting the hydrogenation in the liquid phase in the presence of an active hydrogenation catalyst, under moderate hydrogen pressure such as 2 to 5 atmospheres absolute, and at relatively low temperatures, such as from 0° to 40° C. and even up to 100° C., using substantially less than the stoichiometric amount of hydrogen theoretically required to completely reduce the cyclic diene to the corresponding cyclic monoolefin. The catalyst therein disclosed is a pyrophoric nickel metal catalyst, such as Raney nickel. It is also disclosed that it is desired to conduct the reaction in dilute solution. The dilution may be affected by the addition of any solvent, stable under conditions of the process and which is not a catalyst poison and whose boiling point is such as to render it easily separable from the reaction mixture. Benzene and ethanol, as well as tetralin, dioxane, isooctane, ethyl ether and diisopropyl ether are disclosed as such solvents in such process.

In U.S. Pat. No. 3,819,734, issued July 25, 1974, there is disclosed the hydrogenation of cyclopentadiene to cyclopentene by bringing cyclopentadiene into contact with a catalyst consisting essentially of (1) nickel, on a magnesium or zinc oxalate support, (2) a ligand selected from the group consisting of trimethyl phosphine, triethyl phosphine, methyl ethyl propyl phosphine, trimethyl phosphite, triethyl phosphite, tributyl phosphite, triphenyl phosphite, etc., while in the presence of hydrogen, at temperatures above 0° C. and at pressures from 0 to 1000 pounds per square inch gauge. The solvent mentioned therein is ethanol.

In U.S. Pat. No. 3,994,986, issued Nov. 30, 1976, there is disclosed the preparation of cyclopentene from cyclopentadiene by hydrogenating cyclopentene with hydrogen gas at a ratio of 1 to 1.5 moles of hydrogen per mole of cyclopentadiene in the presence of a palladium catalyst on a carrier.

Also, in U.S. Pat. No. 3,857,894, issued Dec. 31, 1974, there is disclosed the hydrogenation of cyclopentadiene to cyclopentene in the presence of a palladium catalyst and a small amount of an aqueous solution of zinc salt having a water/zinc ratio of at least 1/1 by weight.

It has been found that in order to have a fairly selective hydrogenation of cyclopentadiene to cyclopentene a reaction medium or diluent should be employed.

Certain advantages are inherent in the use of an aqueous medium and surfactants as the reaction medium or diluent. The presence of water aids greatly in moderating the exothermic nature of the hydrogenation of cyclopentadiene. A particular advantage of the present invention in using a surfactant with the water as the reaction medium is that much better hydrogenation rates can be obtained than when surfactants are not employed. Also, cyclopentadiene and cyclopentene are not soluble in the water-surfactant mixture under the operating conditions employed in the present hydrogenation. Consequently, the process of the present invention provides a very effortless method for removal of the aqueous reaction medium from the product mixture containing the cyclopentadiene because there is formed a two-phase system. Still another advantage which may be obtained is that the cyclopentadiene feedstock which has been formed by the steam cracking of dicyclopentadiene may be employed in an undried condition.

The cyclopentadiene employed in the formation of cyclopentene by hydrogenation is usually obtained by cracking or the depolymerization of dicyclopentadiene. To obtain cyclopentadiene from dicyclopentadiene, dicyclopentadiene is heated to a temperature of 150° C. or higher in a conventional cracking apparatus at atmospheric pressure. The depolymerized material should be used in the hydrogenation process without substantial delay. Cyclopentadiene will redimerize upon storage at ambient temperatures for substantial periods of time.

SUMMARY OF THE INVENTION

According to the invention, cyclopentadiene is selectively hydrogenated to cyclopentene in the liquid phase by contacting cyclopentadiene with hydrogen in the presence of a catalyst comprising a highly dispersed form of nickel and in which a substantial amount of water and a small amount of a surfactant is employed as the reaction medium.

The surfactants employed in this invention are not new and cover a wide range of compounds. The surfactants useful in the invention are classified by Bennett, Bishop and Wulfinghoff in "Practical Emulsions", Vol. 1, (1968), published by Chemical Publishing Company, Inc., New York, N.Y. These authors define surfactants as emulsifying agents, foaming agents and protective colloids. Chemically, the authors categorize the surfactants as anionic, cationic, non-ionic, amphoteric, naturally occurring and oil soluble.

These surfactant categories can be further divided into sub-groups which are given to represent examples of surfactants that may be employed in this invention and are not intended to limit the scope in any way of the surfactants which may be employed.

I. Anionic surfactants

A. Sulfates
B. Alkyl and alkylaryl sulfonic acids and their salts
C. Carboxylic acids and their salts II. Cationic Surfactants A. Primary, secondary and tertiary amine salts
B. Quaternary ammonium compounds

III. Non-ionic Surfactants

A. Alkoxy ethers and polyethers
B. Alkoxy esters
C. Amides

IV. Amphoteric Surfactants

A. Amino and carboxy compounds
B. Amino and sulfuric esters
C. Amino and alkyl sulfonic acids
D. Amino and aromatic sulfonic acids
E. Substituted betaines
F. Quaternary phosphoammonium compounds

V. Naturally occurring surfactants

A. Alginates
B. Phospholipids and steroids
C. Lecithin
D. Sterols
E. Water soluble gums
F. Cellulose derivatives

VI. Oil soluble surfactants

A. Organosilicon compounds
B. Fluorocarbons

The following is a list of surfactants suitable for use in this invention. This is intended to be representative but not exhaustive of such surfactants.

Representative examples of anionic surfactants are:
(a) sulfates such as sodium oleyl sulfate and sodium lauryl sulfate;
(b) alkyl and alkylaryl sulfonic acids and their salts such as isopropyl naphthalene sulfonic acid and isobutyl naphthalene sulfonic acid and their sodium salts; dihexyl sodium sulfosuccinate and diamyl sodium sulfosuccinate and their corresponding acids;
(c) carboxylic acids and their salts such as stearic acid and linoleic acid and their sodium salts.

Representative examples of cationic surfactants are:
(a) primary, secondary and tertiary amine salts such as triethanolamine salt of stearic acid and cetyltrimethyl ammonium chloride; morpholine and diethanolamine salts of stearic acid; tris(hydroxymethyl) aminomethane salt of stearic acid and 2-amino-2-methyl-1,3-propanediol salt of stearic acid;
(b) quaternary ammonium compounds such as cetyl pyridinium chloride and trimethyl benzylammonium hydroxide.

Representative examples of nonionic surfactants are:
(a) alkoxy ethers and polyethers such as ethoxylated octyl phenol and oxyethylene polyoxypropylene propylene glycol;
(b) alkoxy esters such as dehydrated sorbitol and diglycol stearate;
(c) amides such as 2-hydroxyethylpalmitamide and 2-hydroxyethylstearamide.

Representative examples of amphoteric surfactants are:
(a) amino and carboxy compounds such as triethanolamine oleate and trihydroxyethylamine stearate;
(b) amino and sulfuric esters such as diethanolamine salt of ricinoleicsulfuric acid;
(c) amino and alkyl sulfuric acids and salts such as dodecylbenzene sulfonate triethanolamine salt;
(d) amino and aromatic sulfonic acids and salts such as triethanolamine salt of naphthalene sulfonic acid;
(e) substituted betaines such as palmityl ester of betaine hydrobromide;
(f) quaternary phosphoammonium compounds such as ammonium butyl phosphate and ammonium propyl phosphate.

Representative examples of naturally occurring surfactants are:
(a) alginates such as sodium alginate and ammonium alginate;
(b) phospholipids and steroids such as egg yolk,
(c) lecithin such as lecithin from soybean oil,
(d) sterols such as cholesterol from lanolin;
(e) water soluble gums such as gum arabic and gum karaya;
(f) cellulose derivatives such as methyl cellulose and hydroxyethyl cellulose.

Representative examples of oil-soluble surfactants are:
(a) organo-silicone compounds such as silicone oil, such as SF-1034, marketed by General Electric Co., Silicone Products Dept., Waterford, N.Y., and DC-200 Silicone oil, marketed by Dow Corning Co., Midland, Mich.;
(b) fluorocarbons such as heptafluorobutoxy polyoxyethylene ethanol and N-ethyl-N-polyoxyethylene ethanol perfluorooctane sulfonamide.

A further representative example of the surfactants useful in this invention is the 0.03 weight percent solution of an amine derivative of an alkyl aryl sulfonate designated as Snoop ™, a registered trademark of Nupro Company, Cleveland, Ohio.

Another is the 40% by weight solution of a fluoro surfactant designed as Zonyl ™ FSC, a registered trademark of E. I. du Pont de Nemours and Company, Wilmington, Del.

Another is the 30% solution of the sodium salt of an octanoic acid derivative of imidazoline, designated as Rewopon AM-V, marketed by Rewo Chemicals Inc., Farmingdale, N.Y.

Another is the 38% by weight solution of the sodium salt of the product of the reaction of imidazoline with methyl and ethyl acrylates followed by hydrolysis and designated Monoteric CEM-38, and marketed by Mona Industries Inc., Patterson, N.J.

Another is Triton X-100 ™ is a polyalkyl ether (alkyl phenoxy polyethoxy ethanol) and a registered trademark of Rohm and Haas Co., Philadelphia, Pa.

Of these, Snoop ™, which is an amine salt of an alkaryl sulfonic acid, and Monoteric CEM-38, which is an amphoteric surfactant and is an amino and a carboxy compound, and Triton X-100 ™, an alkyl phenoxy polyethoxy ethanol, are the preferred surfactants to be used in this invention.

DETAILED DESCRIPTION OF THE INVENTION

The temperature at which cyclopentadiene may be hydrogenated in accordance with this invention may range from 0° to 75° C., with 20° to 30° C. being most preferred. Temperatures that approach 100° C. tend to consume the cyclopentadiene in side reactions, such as dimerizations back to dicyclopentadiene and other undesirable side reactions. Generally speaking, both temperature and the pressure of hydrogen employed should be kept as low as possible consistent with reasonable rates of hydrogenation. When faster rates of reaction than that being obtained are desired, it is preferable to increase the rate of hydrogenation by means of increased hydrogen pressure rather than an increase in the temperature.

High hydrogen pressures may be employed to effect faster rates of hydrogenation; however, it has been found in accordance with the present invention, that about 130 to about 150 psig/about 895.7 to about 1035.5 kPa is all that is required to give a reasonable rate of reaction.

The reaction medium, which is water, is not conducive to the solubility of the cyclopentadiene and thereby renders the process a two-phase system that requires some vigorous agitation. Upon agitation, the water serves as a heat sink by absorbing unwanted heat from the reaction site and, hence, moderating the hydrogenation.

The presence of a two-phase system when the agitation is stopped also offers the advantage that the catalyst settles to the bottom of the lower aqueous layer and no residual hydrogenation of the organic layer occurs if a lengthy time is required to remove the reaction product, cyclopentene. Water also serves to protect the catalyst from air and thereby facilitates an easy recycling of the catalyst.

The catalyst employed in the present invention is a highly dispersed form of nickel. However, a Raney nickel-type catalyst is preferred. Methods for preparing the Raney nickel catalyst which are useful in this invention are known and can be found in a book entitled "CATALYTIC HYDROGENATION", by Robert L. Augstine, published in 1965 by Marcel Dekker, Inc., New York, N.Y.

Temperatures employed to prepare Raney nickel do not vary widely and are disclosed in this reference. The author refers to these Raney nickel catalysts as W1, W2, W3, W4, W5, W6, W7 and W8. In addition to the W-type Raney nickel, a Raney nickel referred to as T-1 is preferred, or a modification of T-1 Raney nickel is preferred.

In the Journal of Organic Chemistry 26, 1625 (1961), there is described a process for the preparation of what the authors refer to as T-1 Raney nickel by Dominguez, Lopez and Franco. In this article, the authors state that the preparation of the T-1 Raney nickel catalyst is a modification of the procedure described by Papa, Schwenk and Whitman in the Journal of Organic Chemistry 7, 586, (1942) and Papa, Schwenk and Brieger in the Journal of Organic Chemistry, 14, 366, (1949). All of the Raney nickels described in the articles referred to above are operable in the process of this invention.

Other nickel catalysts useful in the invention can be obtained by the use of new techniques known to the catalyst art for depositing metals on suitable supports in a highly dispersed form. These nickel catalysts would exhibit catalytic properties similar to the properties exhibited by the Raney nickel catalysts.

In the article by Dominguez et al, the authors state that the T-1 Raney nickel was prepared as follows:

To a 1-liter 3-neck flask containing 600 ml of a 10 percent sodium hydroxide solution, 40 grams of Raney nickel aluminum alloy (50 percent nickel) were added in small portions over a period of 20 to 30 minutes with mechanical stirring. The temperature was kept at 90°–95° C. during this addition. The mixture was stirred for an additional hour period at which time the stirring was stopped and the nickel was allowed to settle, and the solution decanted. The metal was washed five times with 200-ml portions of water and then five times with 50-ml portions of ethanol in such a manner that the nickel was always covered with liquid. The catalyst was then stored under ethanol and refrigerated for further use.

The Raney nickel employed in some of the examples of this invention and termed by the present inventor as Modified T-1 Raney nickel, was prepared by a slight modification of Dominguez et al's procedure as follows:

A solution of 2 grams of sodium hydroxide in 50 ml of water was heated to its boiling point and then there was added 2 grams of Raney nickel aluminum alloy (1 gram of Raney nickel) as rapidly as the hydrogen evolution would permit. This mixture was then digested at 95° to 100° C. for $\frac{1}{4}$ hour (reflux) and the water was continually replaced as it evaporated. The solution was decanted from the Raney nickel and the metal washed with three 250-ml portions of cold water. This catalyst was employed without washing with ethanol.

The ratio of catalyst to cyclopentadiene is not too critical. It has been found satisfactory results are obtained when about 1 part by weight of catalyst per 500 parts by weight of cyclopentadiene are employed. When a catalyst to cyclopentadiene weight ratio greater than about 1 to 33 is employed, the catalyst is being wasted.

The amount of water employed should be substantial and should range from about a volume ratio of water to cyclopentadiene of about 1/1 to about 4/1.

The amount of surfactant used in this invention will depend largely on the type and the concentration of the particular surfactant. It has been determined that a surfactant to water weight ratio from about 1/3000 to about 1/300,000 will give good results in this hydrogenation system. If an insufficient amount of surfactant is employed, there is a tendency to slow the hydrogenation reaction. On the other hand, too much surfactant tends to lower the selectivity to the product cyclopentene and also is wasteful.

Therefore, anyone skilled in the art would be able to determine the optimum amount of surfactant in which to employ in the practice of the present invention. It should be realized that, due to the wide variety of surfactants which may be employed, the molecular weights of the various surfactants generally are very different. These factors should be taken into consideration in attempting to determine the optimum amount of surfactant to use. For instance, using a non-ionic surfactant such as Triton X-100 TM in about 300 ml of water, it has been found that from about 0.05 to about 0.25 ml of surfactants give good results; whereas using the same amount of water and Snoop TM requires 8 ml of Snoop TM (which is, in essence, only 0.0024 ml of active surfactant, the Snoop TM being only available in a 0.03 weight percent solution) to produce similar results.

The practice of this invention is further illustrated by reference to the following examples which are intended to be representative rather than restrictive of the scope of the invention. Unless otherwise indicated, all parts and percentages are by weight.

EXAMPLE 1

The following examples were run in a one liter stainless steel reactor which was swept with nitrogen and charged with 305 milliliters (ml) of water to which was added the surfactants in the amounts as set forth in Table 1. The catalyst employed in each of the runs, unless otherwise noted, was 1.0 gram of modified T-1 Raney nickel. In each of the runs, unless otherwise noted, 66 grams of cyclopentadiene containing 5 grams of pentane as an internal chromatographic standard was then charged under nitrogen to the reactor. The reactor was sealed and charged with 150 psig of hydrogen, unless otherwise noted, while the mixture was being agitated. The reaction temperature was held at 25° C. by means of internal cooling coils. When the calculated one molar equivalent of hydrogen per mole of cyclopentadiene had been consumed, the stirring was stopped and the catalyst separated out. The organic and aqueous phases were separated within a few minutes. The top layer, the organic phase, was drawn out of the reactor, via a dip leg and diluted with alcohol for chromatographic analysis.

In Run #13, the original hydrogen pressure employed was 1722.5 kPa—250 psig. In Run #14, the hydrogen pressure employed was 3100.5 kPa—450 psig. In the table below the remaining operating conditions and results are set forth. In this table "Rx Time" is the reaction time; "Conv CPD" is conversion of cyclopentadiene; "Sel CPE" is selectivity to cyclopentene; and "Sel CPA" is selectivity to cyclopentane.

Table 1

| Run No | Surfactant | Amt | Rx Time (min) | Conv CPD (%) | Sel CPE (%) | Sel CPA (%) |
|---|---|---|---|---|---|---|
| | NONIONIC | | | | | |
| 1 | Triton X-100® | 0.50 ml | 42 | 77.2 | 78.0 | 5.1 |
| 2 | Triton X-100® | 0.25 ml | 53 | 89.4 | 94.6 | 5.0 |
| 3 | Triton X-100® | 0.05 ml | 63 | 96.2 | 95.0 | 5.0 |
| 4 | Triton X-100® | 0.005 ml | 65 | 78.0 | 93.0 | 1.2 |
| 5 | Triton X-100® | 0.005 ml | 95 | 92.5 | 93.4 | 4.8 |
| | ALKALI METAL SOAP | | | | | |
| 6 | K stearate | 0.50 g | 60 | 23.8 | 57.6 | 2.1 |
| 7 | K stearate | 0.10 g | 60 | 41.0 | 78.3 | 0.4 |
| 8 | K stearate | 0.01 g | 35 | 96.4 | 83.9 | 12.5 |
| | NON-ALKALI METAL SOAP | | | | | |
| 9 | Zn Stearate | 0.01 g | 59 | 91.7 | 96.8 | 2.3 |
| 10 | Snoop® | 8.0 ml | 41 | 79.2 | 98.0 | 1.8 |
| 11 | Snoop® | 8.0 ml | 52 | 85.0 | 94.4 | 2.2 |
| 12 | Snoop® | 8.0 ml | 61 | 94.5 | 94.4 | 5.0 |
| 13 | Snoop® | 8.0 ml | 28 | 83.0 | 95.0 | 2.5 |
| 14 | Snoop | 8.0 ml | 15 | 83.0 | 89.3 | 4.7 |
| | CATIONIC SURFACTANT | | | | | |
| 15 | benzyltrimethyl-ammonium hydroxide | 0.10 ml | 86 | 92.0 | 91.4 | 8.8 |
| 16 | benzyltrimethyl-ammonium hydroxide | 1.00 ml | 65 | 91.0 | 91.3 | 8.8 |

EXAMPLE 2

The following hydrogenations were run in a one liter stainless steel reactor which was swept with nitrogen and charged with 150 ml of water to which was added the surfactants in amounts as set forth in Table 2. The catalyst employed in each of the runs, unless otherwise noted, was 1.0 gram of modified T-1 Raney nickel. In each of the runs, unless otherwise noted, 33 grams of cyclopentadiene containing 5 grams of pent ne as an internal chromatographic standard was then charged under nitrogen to the reactor. The reactor was sealed and charged with 2067 kPa—300 psig of hydrogen while the mixture was being agitated. The reaction temperature was held at 25° C. When the calculated one molar equivalent of hydrogen per mole of cyclopentadiene had been consumed, the stirring was stopped and the catalyst separated out. The organic and aqueous phase was separated. The top layer, the organic phase was subjected to chromatographic analysis. In Run #7, the temperature was maintained at 18° C. In #8, the temperature was maintained at 30° C. In Run #10 and Run #11, 42 ml of water, instead of 150 ml, were employed. The symbols in the columns are the same as for Example 1.

Table 2

| Run No | Surfactant | Amt | Rx Time (min) | Conv CPD (%) | Sel CPE (%) | Sel CPA (%) |
|---|---|---|---|---|---|---|
| 1 | | 0.0 | 45 | 93.6 | 88.4 | 11.5 |
| 2 | Zonyl® | 0.1 ml | 40 | 89.0 | 84.9 | 15.0 |
| 3 | Snoop® | 2.0 ml | 34 | 98.4 | 87.9 | 12.0 |
| 4 | Snoop® | 3.0 ml | 25 | 97.2 | 92.0 | 7.5 |
| 5 | Snoop® | 4.0 ml | 20 | 96.4 | 95.2 | 4.6 |
| 6 | Snoop® | 5.0 ml | 20 | 99.5 | 90.7 | 9.0 |
| 7 | Snoop® | 4.0 ml | 23 | 93.8 | 95.5 | 4.0 |
| 8 | Snoop® | 4.0 ml | 18 | 95.4 | 90. | 8.6 |
| 9 | dil NaOH | 1.0 g | 34 | 90.2 | 89.4 | 10.0 |
| 10 | Snoop® | 4.0 ml | 33 | 98.6 | 82.7 | 17.0 |
| 11 | Snoop® | 2.0 ml | 59 | 97.3 | 89.6 | 9.8 |
| 12 | xylene sulfonate salt | 2.0 ml | 22 | 89.0 | 84.7 | 12.9 |
| 13 | xylene sulfonate salt | 4.0 ml | 27 | 91.3 | 88.0 | 11.8 |
| 14 | xylene sulfonate salt | 8.0 ml | 28 | 90.0 | 85.9 | 14.0 |
| 15 | Monateric® | 1.0 ml | 35 | 96.8 | 91.2 | 8.4 |
| 16 | Monateric® | 0.5 ml | 27 | 98.2 | 95.0 | 4.5 |
| 17 | Monateric® | 0.25 ml | 28 | 94.4 | 94.7 | 5.1 |
| 18 | Rewopon | 0.5 ml | 33 | 99.6 | 88.7 | 11.0 |

EXAMPLE 3

In a one-liter stainless steel reactor which was swept with nitrogen and charged with 150 ml of water to which had been added 4.0 ml of Snoop ™. The catalyst employed was 1.0 gram of W2 Raney nickel. 33 grams of cyclopentadiene containing 5.0 grams of pentane as an internal chromatographic standard was then charged under nitrogen to the reactor. The reactor was sealed and charged with 300 psig—2067 kPa of hydrogen and the mixture was then agitated. The reaction temperature was controlled at 25° C. When one molar equivalent of hydrogen per mole of cyclopentadiene had been consumed (about 21 minutes), the stirring was stopped. The organic and aqueous phase separated within a few minutes. The top layer, the organic layer, was drawn out of the reactor and chromatographic analysis made. The analysis revealed a 98.7% conversion of the CPD, a 91.0% selectivity to CPE and a 8.6% selectivity to CPA.

While certain representative embodiments and details have been shown for the purpose of illustrating the invention, it will be apparent to those skilled in this art that various changes and modifications may be made therein without departing from the spirit or scope of the invention.

What is claimed is:

1. In a process for the preparation of cyclopentene which comprises selectively hydrogenating cyclopentadiene in the liquid phase by contacting cyclopentadiene with hydrogen in the presence of a catalyst comprising a highly dispersed form of nickel selected from the group of Raney nickel and modified Raney nickel, the improvement comprising using as the reaction medium water and a surfactant selected from the group consisting of anionic, cationic, non-ionic, amphoteric, naturally occurring and oil soluble surfactants, the ratio of water to cyclopentadiene ranging from about 1/1 to about 4/1 and the surfactant to water weight ratio ranging from about 1/3000 to about 1/300,000.

2. The process according to claim 1 in which the pressure of the hydrogen is at least 1035.5 kPa—150 psig.

* * * * *